United States Patent [19]

White et al.

[11] 4,267,274

[45] May 12, 1981

[54] *STREPTOMYCES MEDITERRANEI* MUTANT CAPABLE OF PRODUCTION OF RIFAMYCIN B

[75] Inventors: Richard J. White, Como; Giancarlo Lancini, Pavia, both of Italy

[73] Assignee: Gruppo Lepetit S.p.A., Milan, Italy

[21] Appl. No.: 479,018

[22] Filed: Jun. 13, 1974

Related U.S. Application Data

[62] Division of Ser. No. 354,811, Apr. 26, 1973, Pat. No. 3,871,965.

[51] Int. Cl.³ .......................... C12N 1/20; C12R 1/465
[52] U.S. Cl. ...................................... 435/253; 435/886
[58] Field of Search .............. 195/80 R; 435/253, 886

[56] References Cited

U.S. PATENT DOCUMENTS 3,150,046  9/1964  Sensi et al. .......................... 195/80 X

OTHER PUBLICATIONS

Martin Frolisher; *Fundamentals of Microbiology*; p. 185 8th edition (1968).

*Primary Examiner*—Robert J. Warden

[57] ABSTRACT

A biologically pure culture of *Streptomyces mediterranei*, mutant strain 18, ATCC

2 Claims, No Drawings

STREPTOMYCES MEDITERRANEI MUTANT CAPABLE OF PRODUCTION OF RIFAMYCIN B

This is a division of application Ser. No. 354,811 filed Apr. 26, 1973 now U.S. Pat. No. 3,871,965.

BACKGROUND OF THE INVENTION

It has previously been reported that during fermentation in normal growth media, *Streptomyces mediterranei* synthesizes a family of antibiotics collectively referred to as the rifamycin complex (P. Sensi, et al., Antibiotics Annual 1959-1960, page 262). Subsequent work revealed that the addition of sodium diethyl barbiturate to the culture medium resulted essentially in the formation of a single fermentation product, rifamycin B (Margalith P. and Pagani H., Applied Microbiology, 9, 325, 1961).

SUMMARY OF THE INVENTION

The present invention relates to the isolation of a mutant strain of *Streptomyces mediterranei* and the elaboration by it of essentially rifamycin B only, irrespective of the presence or absence of sodium diethyl barbiturate in the fermentation medium, so that an improved process for making rifamycin B results. The rifamycin B is recovered from the fermentation medium in a conventional manner.

DESCRIPTION OF SOME PREFERRED EMBODIMENTS

The following is a written description of the invention and of the manner and process of making and using it to enable the art skilled to make and use the same and sets forth the best mode contemplated by the inventors of carrying out their invention.

Isolation of Mutant Strain

A suspension of spores of *Streptomyces mediterranei* ATCC 13685 was treated with N-methyl-N'-nitroso-N-nitroguanidine at 1 mg/ml in a pH 9.0 tris(hydroxymethyl)aminomethane buffer for 60 minutes at 28° C. The mutagen-treated spores were then washed and plated onto Petri dishes containing Bennett agar. After 14 days incubation at 28° C., the surviving colonies were picked off and examined for their ability to produce rifamycin B in liquid medium with and without sodium diethyl barbiturate. The mutant producing high quantities of rifamycin B in the absence of sodium diethyl barbiturate was further examined. Such mutant was called M 18 and deposited with the ATCC under the number 21789 and its characteristics will be described later in detail.

Fermentation

An industrial strain of *Streptomyces mediterranei* ATCC 13685 and strain M 18 were propagated on Bennett agar for 6 to 8 days at 28° C. The vegatative medium was inoculated with a slant of Bennett agar (½ slant per flask) and the flasks were incubated on a rotary shaker at 28° C. for 72 hours. The vegetative medium used contained:

| | |
|---|---|
| Beef extract | 5 g. |
| Yeast extract | 5 g. |
| Poptone | 5 g. |
| Gasein hydrolyzate | 3 g. |
| NaCl | 1.5 g. |
| H$_2$O to make | 1 liter |

The pH was adjusted to 7.3 with NaOH. An amount of 100 ml. vegetative medium was used in 500 ml. Erlenmeyer flasks. After 72 hours growth the vegetative medium was used to inoculate (5% v/v) the fermentation medium.

Two fermentation media were used:
RFB 744: a synthetic medium
RFB 2244: a complex medium Fermentation were always carried out using 50 ml. of medium in a 500 ml. Erlenmeyer flask.

The composition of the two media was as follows:

| RFB 744 | |
|---|---|
| Glucose | 96 g. |
| (NH$_4$)$_2$SO$_4$ | 15 g. |
| KH$_2$PO$_4$ | 2 g. |
| MgSO$_4$ . 7H$_2$O | 1 g. |
| CaCO$_3$ | 17 g. |
| CuSO$_4$ . 5H$_2$O | 0.0033 g. |
| FeSO$_4$ . 7H$_2$O | 0.01 g. |
| ZnSO$_4$ . 7H$_2$O | 0.05 g. |
| MnSO$_4$ . 4H$_2$O | 0.04 g. |
| CoCl$_2$ . 6H$_2$O | 0.002 g. |
| (NH$_4$)$_6$Mo$_7$O$_{24}$ . 4H$_2$O | 0.001 g. |
| Sodium diethyl barbiturate | 2 g. |
| H$_2$O | 1000 ml. |
| pH before sterilizing | 6.8 |
| pH after sterilizing | 6.3 |
| RFB 2244 | |
| Glucose | 126.5 g. |
| Propylene glycol | 5 g. |
| CaCO$_3$ | 9.5 g. |
| Peanut flour | 25 g. |
| Soybean flour | 10 g. |
| (NH$_4$)$_2$SO$_4$ | 1 g. |
| MgSO$_4$ . 7H$_2$O | 1 g. |
| FeSO$_4$ . 7H$_2$O | 0.01 g. |
| CuSO$_4$ . 5H$_2$O | 0.0033 g. |
| ZnSO$_4$ . 7H$_2$O | 0.050 g. |
| MnSO$_4$ . 5H$_2$O | 0.004 g. |
| CoCl$_2$ . 6H$_2$O | 0.002 g. |
| (NH$_4$)$_6$Mo$_7$O$_{24}$ . 4H$_2$O | 0.001 g. |
| Sodium diethyl barbiturate | 1.5 g. |
| pH before sterilization corrected with 15% NaOH | 7.4 |
| pH after sterilization | 6.2-6.3 |
| Antifoam A silicone defoamer | 0.2 ml. per flask containing 50 ml. of growth medium |

The same media were prepared without the addition of sodium diethyl barbiturate to carry out comparative fermentations. The fermentation conditions and rates are given in Tables 1 and 2 together with the obtained rifamycin B yields.

TABLE 1

| | Rifamycin B in medium, 82 g/ml | |
|---|---|---|
| Strain | with barbiturate | without barbiturate |
| *Streptomyces mediterranei* ATCC 13685 | 2210 | <390* |
| Mutant M 18 ATCC 21789 | 2290 | 2240 |

The fermentation medium used was RFB 2244 with and without 1.5 g. of sodium diethyl barbiturate per liter at a temperature of 28° C. and a fermentation period of 190 hours.
*This result represents an upper limit for the amount of rifamycin B present, as the presence of rifamycin complex in the comparative medium interferes with the normal assay.

TABLE 2

| Strain | Rifamycin B (μg/ml) with barbiturate | Rifamycin B (μg/ml) without barbiturate | Rifamycin complex (μg/ml) with barbiturate | Rifamycin complex (μg/ml) without barbiturate |
|---|---|---|---|---|
| Streptomyces mediterranei ATCC 13685 | 344 | <107 | <10 | 99 |
| Mutant M 18 ATCC 21789 | 580 | 513 | <10 | <10 |

The fermentation medium used was RFB 744 with and without 1.5 g. per liter of sodium diethyl barbiturate. Fermentation time was 144 hours at 28° C. on a rotary shaker.

Assay of Rifamycin B

The rifamycin B content of the filtered broths was assayed by a differential spectrophotometric technique described by Pasqualucci, et al., Journal of Pharmaceutical Sciences 59, 685, 1970.

Estimation of Rifamycin Complex

Samples of fermentation medium were adjusted to pH 2.0 with hydrochloric acid and extracted with ethyl acetate. The organic extract was then extracted with the phosphate buffer, pH 7.38; under these conditions rifamycin B is extracted by the buffer whereas the rifamycin complex remains in the exhausted organic phase. The rifamycin complex in the exhausted ethyl acetate was estimated spectrophotometrically by measuring the optical density at 460 m$\mu$ of an aliquot suitably diluted in ethyl alcohol containing 1% ascorbic acid.

In industrial practice, the product rifamycin B is recovered from a fermented broth in usual ways.

Description of Streptomyces Mediterranei M 18 ATCC 21789

For the investigation of growth characteristics, *Str. mediterranei* and its mutant strain M 18 were grown in a variety of standard media according to Gottlieb and Shirling, (Methods of Characterization of Streptomyces Species, Intern. J. Syst. Bact. 16, 313–340, 1966); and, in addition, some media recommended by Waksman were used (The Actinomycetes, Vol. II, Williams and Wilkins Co., 1961).

The following Tables report the growth characteristics and properties of the mutant strain M 18 ATCC 21789 and of *Streptomyces mediterranei* ATCC 13685.

TABLE 3

Assimilation of carbon compounds by streptomyces mediterranei and mutant M 18

| Carbon Sources | Streptomyces mediterranei ATCC 13685 | Mutant M 18 ATCC 21789 |
|---|---|---|
| Inositol | ++ | ++ |
| Fructose | ++ | ++ |
| Rhamnosed | ++ | ++ |
| Xylose | ++ | ++ |
| Raffinose | − | − |
| Arabinose | ++ | ++ |
| Cellulose | − | − |
| Sucrose (positive control) | ++ | ++ |
| No carbon (negative control) | − | − |

TABLE 4

Comparison of morphologic and growth properties of *Streptomyces mediterranei* ATCC 13685 and mutant M 18 ATCC 21789

| Media | *Streptomyces mediterranei* ATCC 13685 | *Streptomyces mediterranei* M 18 ATCC 21789 |
|---|---|---|
| Oat meal agar | Fair growth with smooth surface. Vegetative mycelium hyaline to yellowish with pinkish reverse. Whitish aerial mycelium with pinkish reverse. Traces of yellowish soluble pigment. | Abundant growth with smooth surface. Vegetative mycelium greenish to orange with amber shadow. Aerial mycelium absent. Yellow green soluble pigment. |
| Yeast extract glucose agar (medium No. 2 Gottlieb and Shirling) | Abundant growth yellowish to pink with rough surface. Scanty aerial mycelium. No pigmentation of medium. | Abundant growth with wrinkled surface. Vegetative mycelium amber brown with orange brown edges. Traces of pinkish aerial mycelium. Deep amber brown soluble pigment. |
| Emerson glucose agar | Abundant growth, yellowish to pink orange with rough surface. Scanty aerial mycelium becomes pinkish. No pigmentation of medium. | Abundant growth with smooth surface. Orange vegetative mycelium. No aerial mycelium. Golden yellow soluble pigment. |
| Bennett's agar | Good growth, yellowish turning orange yellow. Aerial mycelium becoming pinkish. Light amber pigment. | Abundant growth with very wrinkled surface. Vegetative mycelium amber brown with orange brown edges. Traces of pinkish aerial mycelium. Deep amber brown soluble pigment. |
| Penassay agar | Poor growth. | Abundant growth with thin and smooth surface. Vegetative mycelium light orange. No aerial mycelium. Traces of light yellow soluble pigment. |
| Pridham's agar | Moderate growth; smooth, colorless with lobster red spots. Pink aerial mycelium. No pigmentation of medium. | Abundant growth with smooth surface. Vegetative mycelium light orange with small patches of brick red color. Traces of pink aerial mycelium. Yellow soluble pigment. |
| Starch agar (Medium No. 4 Gottlieb and Shirling) | Poor growth, colorless to light orange pink. Scarce white aerial mycelium. Starch hydrolysis: doubtful. | Abundant growth with smooth surface. Vegetative mycelium deep orange with brownish tinge. Abundant pink aerial mycelium. Chrome yellow soluble pigment. Starch hydrolysis: negative. |
| Dextrose tryptone agar | Abundant growth, orange pink with golden yellow to orange reverse. Pinkish aerial mycelium. Light golden yellow soluble pigment. | Abundant growth with wrinkled surface. Orange vegetative mycelium. No aerial mycelium. Yellow soluble pigment. |
| Hickey's and Tresner's cobalt agar | Moderate growth, hyaline to light pinkish orange. Some pinkish aerial mycelium. Some yellowish soluble | Abundant growth with smooth surface. Vegatative mycelium amber rose. Traces of pinkish aerial mycelium. Amber rose |

TABLE 4-continued

Comparison of morphologic and growth properties of *Streptomyces mediterranei* ATCC 13685 and mutant M 18 ATCC 21789

| Media | *Streptomyces mediterranei* ATCC 13685 | *Streptomyces mediterranei* M 18 ATCC 21789 |
|---|---|---|
| | pigment. | soluble pigment. |
| Tyrosine agar (Medium No. 7 Gottlieb and Shirling) | Poor growth. | Abundant growth with wrinkled surface. Vegetative mycelium deep orange with brownish tinge. Aerial mycelium absent. Yellow soluble pigment. Tyrosinase reaction: strongly positive. |
| Ca malate agar | Fair growth, colorless. Aerial mycelium whitish with pink tinge. No soluble pigment. Partial digestion of Ca malate. | Fair growth with smooth surface Vegetative light orange mycelium. No aerial mycelium. Light lemon yellow soluble pigment. Scarce digestion of Ca malate. |
| Gelatine | No pigmentation. Liquefaction: slow and incomplete. | No pigmentation. Liquefaction: positive. |
| Yeast extract molasses agar | Abundant rough growth colorless to yellowish, whitish aerial mycelium. Deep amber soluble pigment. | Abundant growth with a very wrinkled surface. Vegetative mycelium burnt brown with orange brown edges. Traces of pink aerial mycelium. Deep yellow ochre soluble pigment. |
| Czapek-Dox glucose agar | Poor growth, thin and colorless to light melon. Traces of pinkish white aerial mycelium. No soluble pigment. | Abundant growth with smooth surface. Vegetative mycelium light orange. No aerial mycelium. Light lemon yellow soluble pigment. |
| Potato agar | Poor growth, thin and colorless. Traces of Whitish aerial mycelium. No soluble pigment. | Abundant growth with smooth surface. Amber rose vegetative mycelium. |
| Glucose asparagine agar | Fair growth with smooth surface. Thin vegetative mycelium of light orange pink color and yellowish reverse. No aerial mycelium. Some light yellow soluble pigment. | Abundant growth with smooth surface. Orange vegetative mycelium. No aerial mycelium. Traces of lemon yellow soluble pigment. |
| Asparagine agar (Medium No. 5 Gottlieb and Shirling) | Fair growth with smooth surface. Thin vegetative mycelium of light orange pink color and yellowish reverse. No aerial mycelium. Some light yellow soluble pigment. | Abundant growth with thin and smooth surface. Light orange vegetative mycelium. No aerial mycelium. No soluble pigment. |
| Nutrient agar | Moderate growth with smooth surface; melon to orange with yellowish orange reverse. Aerial mycelium pinkish white. Soluble pigment absent. | Abundant growth with smooth surface. Orange vegetative mycelium. No aerial mycelium. Light yellow soluble pigment. |
| Nitrate broth | Surface growth with pinkish aerial mycelium. No reduction to nitrites. Broth becomes yellowish. | Surface growth with pinkish aerial mycelium. Reduction of nitrates. Broth becomes yellowish. |
| Litmus milk | No peptonization or coagulation. Slight alkaline reaction. | No coagulation, no peptonization. |
| Skim milk agar | Abundant growth with smooth surface. Vegetative mycelium orange. Cascin hydrolysis; positive. Pink aerial mycelium. No soluble pigment. | Abundant growth with smooth surface. Vegetative mycelium orange. Golden yellow soluble pigment. No aerial mycelium. Casein hydrolysis: strongly positive. |
| Peptone-yeast extract iron agar (Medium No. 6 Gottleib and Shirling) | Moderate growth with smooth surface. Colorless vegetative mycelium. Traces of whitish aerial mycelium. No soluble pigment. H$_2$S production: negative. | Moderate growth with thin and smooth surface. Colorless vegetative mycelium. No aerial mycelium. No soluble pigment. H$_2$S production: negative. |

NOTE:
Color determination was performed using the method of Maerz and Paul, Dictionary of Color, McGraw-Hill, Inc., N.Y., 1950.

We claim:

1. A biologically pure culture comprising a new microorganism mutant identified as *Streptomyces mediterranei* M 18, ATCC 21789, and a nutrient medium consisting essentially of an assimilable carbon source, an assimilable nitrogen source and essential mineral salts, said culture being capable of producing rifamycin B in a recoverable quantity upon fermentation.

2. A biologically pure culture of *Streptomyces mediterranei*, mutant strain 18, (ATCC 21789) capable of producing rifamycin B in a recoverable quantity upon fermentation.

* * * * *

UNITED STATES PATENT AND TRADEMARK OFFICE
CERTIFICATE OF CORRECTION

PATENT NO. : 4,267,274
DATED : May 12, 1981
INVENTOR(S) : Richard J. White, et al.

It is certified that error appears in the above–identified patent and that said Letters Patent are hereby corrected as shown below:

First page, under ABSTRACT second line, "ATCC" should read --ATCC 21789--.

Column 2, Table 1, "82 g/ml" should read --µg/ml--.

Signed and Sealed this

Fifteenth Day of December 1981

[SEAL]

Attest:

GERALD J. MOSSINGHOFF

Attesting Officer

Commissioner of Patents and Trademarks